United States Patent [19]

Tressel

[11] 4,201,408
[45] May 6, 1980

[54] CONTACT LENS INSERTION AND REMOVAL DEVICE

[76] Inventor: Willard Tressel, 667 Cragmont Ave., Berkeley, Calif. 94708

[21] Appl. No.: 878,245

[22] Filed: Feb. 16, 1978

[51] Int. Cl.² ............................................... A61F 9/00
[52] U.S. Cl. .................................................. 294/1 CA
[58] Field of Search .................... 294/1 CA, 64 R, 93, 294/99 R; 128/303 R, 233, 249

[56] References Cited

U.S. PATENT DOCUMENTS

| | | | |
|---|---|---|---|
| 3,129,971 | 4/1964 | Kobler | 294/1 CA X |
| 3,791,689 | 2/1974 | Boone et al. | 294/1 CA |
| 3,897,968 | 8/1975 | Allen | 294/1 CA |
| 3,910,618 | 10/1975 | Massenz | 294/1 CA |
| 3,934,914 | 1/1976 | Carruthers | 294/1 CA |
| 4,026,591 | 5/1977 | Cleaveland | 294/1 CA |
| 4,037,866 | 7/1977 | Price | 294/1 CA |
| 4,082,339 | 4/1978 | Ross | 294/99 R X |

Primary Examiner—Johnny D. Cherry

[57] ABSTRACT

A contact lens insertion and removal device is provided having a cup or similar concave assembly for receiving the lens with a light path for providing a light through the cup and device for applying vacuum or pressure to the cup. Additionally, an arm can be provided for distorting the cup to distort the lens, breaking the bond between the lens and the eye. The device is suitable for use with hard, soft or other contact lenses or may be used with plastic eye bandages.

2 Claims, 10 Drawing Figures

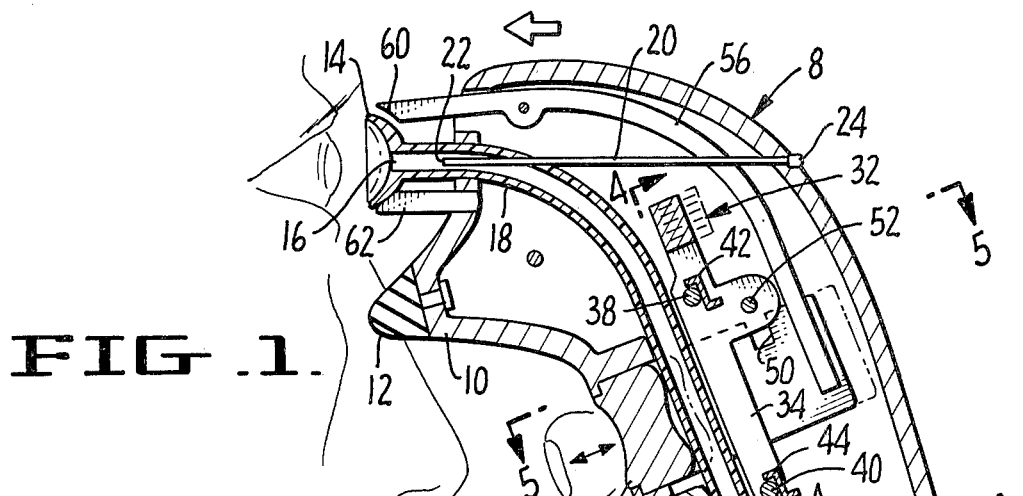
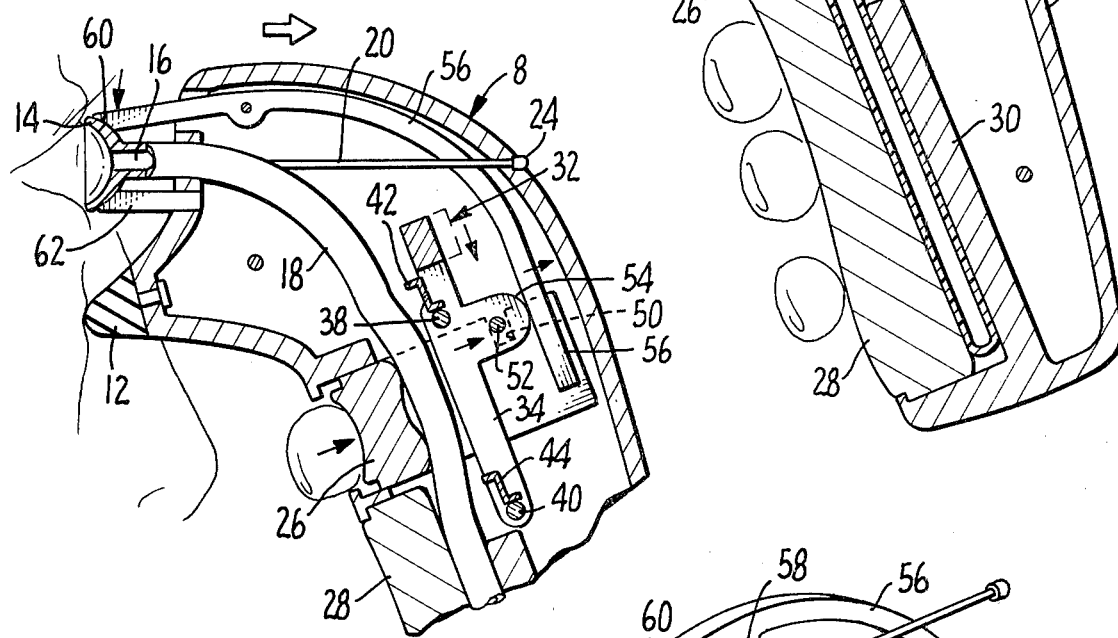
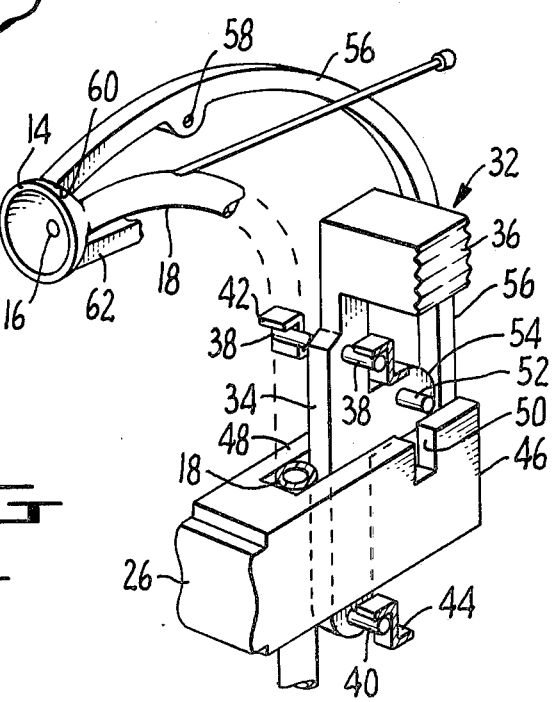
FIG. 1.
FIG. 2.
FIG. 3.

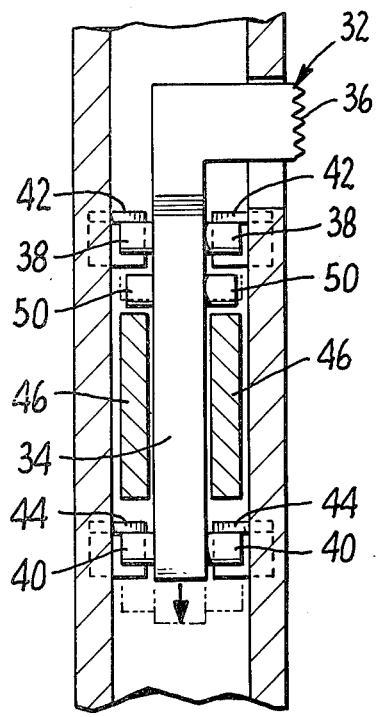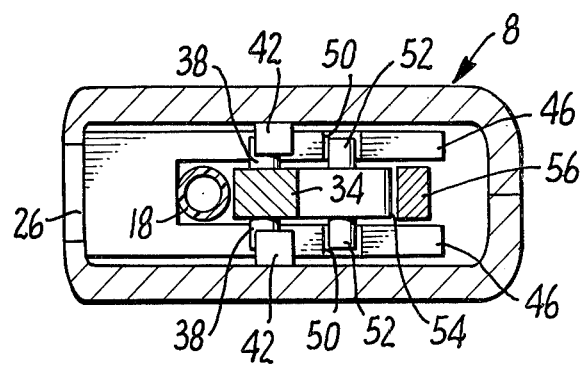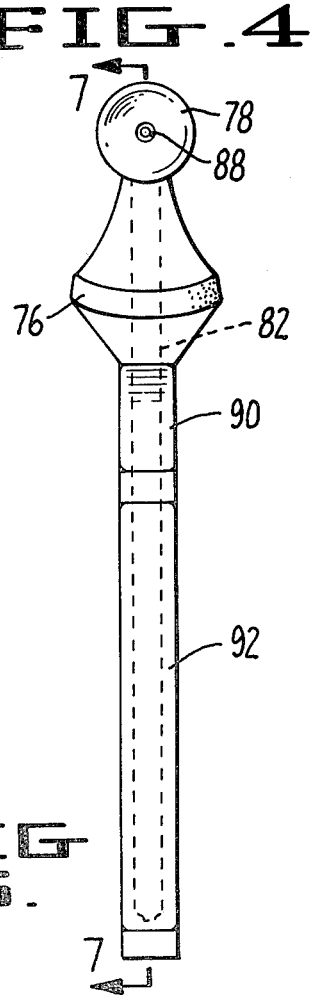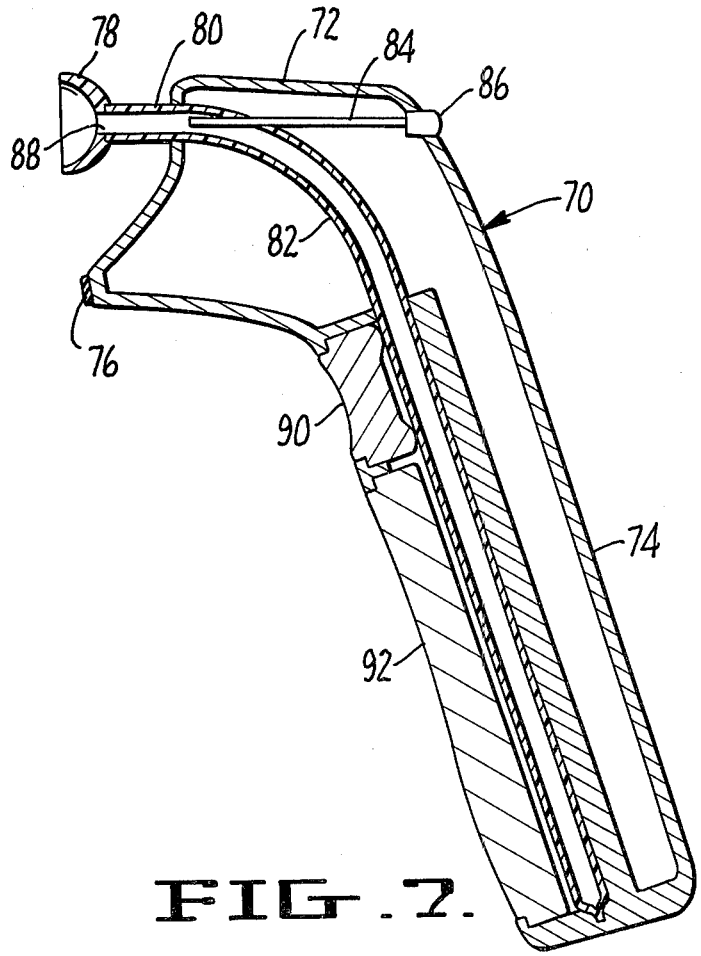

CONTACT LENS INSERTION AND REMOVAL DEVICE

SUMMARY OF THE INVENTION

The present invention relates to a device which, in its simplest form, is suitable for inserting contact lenses. Although the device was particularly designed for use for soft contact lenses, it may also be used with hard contact lenses.

The insertion and removal of contact lenses is frequently difficult, particularly in the case of soft contact lenses which are normally inserted by hand while attempting to keep the convex surface of the lens balanced on the opposed convex surface of a finger. The insertion of such lenses is particularly difficult in the case of aphakic patients such as those whoe have undergone surgery for cataracts. The insertion and removal of the lens is physically cumbersome and time consuming. There is a high probability of dropping the lens, leading to contamination and damage to the lens and even under ideal conditions, there is always the possibility that the finger will convey contamination to the lens. Also, when doing the operation by hand, the possibility of carrying dust or an eyelash into the eye is increased. Similar problems are encountered with plastic eye bandages.

In accordance with the present invention, a contact lens insertion or removal tool is provided which has a lens receiving cup of a proper size to receive the contact lens, the cup being made of a soft, yieldable plastic material. In the center of the cup, a hole is formed leading to a tube which serves a two-fold purpose. In the first place, the tube provides a means for applying vacuum to the cup in order to pick up the lens and subsequently pressure to discharge the lens from the cup onto the eyeball. Further, a light source is provided within the tube which produces a bright spot of light which serves as a target for the user so that even an aphakic patient will have no difficulty in inserting the lens.

As a further aid for the insertion of the lens, the device of the present invention incorporates a cheek rest so that the device can be steadied against the cheek with the cup slightly separated from the eye and then gently rotated into place for the insertion or removal of the lens. This is particularly important since aphakic patients are frequently elderly and have some difficulty in maintaining sufficient steadiness for the insertion or removal of the lens.

In its simplest form, the device of the present invention incorporates only a light beam means and the means for maintaining pressure or vacuum within the tube as described above. In a preferred embodiment of the invention, the removal operation of the lens is facilitated by providing a means which distorts the lens holding cup and the lens, greatly increasing the efficiency of the lens removal aspects of the tool.

In accordance with another aspect of the invention, a novel locking mechanism is provided so that a lever means can be locked in or out of position so that in one position the cup collapsing device is rendered inoperative while in a second position it is operative.

In another embodiment the mechanism is replaced by hydraulic or pneumatic means for distorting the holding cup.

Various other objects and features of the invention will become apparent in the balance of the specification.

DESCRIPTION OF THE PREFERRED EMBODIMENTS

FIG. 1 is a side view, in section, of a preferred embodiment of the invention.

FIG. 2 is a partial view of the device shown in FIG. 1 showing the position of the parts when the lens cup is distorted.

FIG. 3 is a partial view of the internal parts of the device shown in FIG. 1 with certain of the parts omitted for clarity.

FIG. 4 is an enlarged section on the line 4—4 of FIG. 1.

FIG. 5 is an enlarged section on the line 5—5 of FIG. 1.

FIG. 6 is a front view of a simplified form of the device, particularly adapted for use as an insertion tool.

FIG. 7 is a section on the line 7—7 of FIG. 1.

DESCRIPTION OF THE PREFERRED EMBODIMENTS

Figure 8:
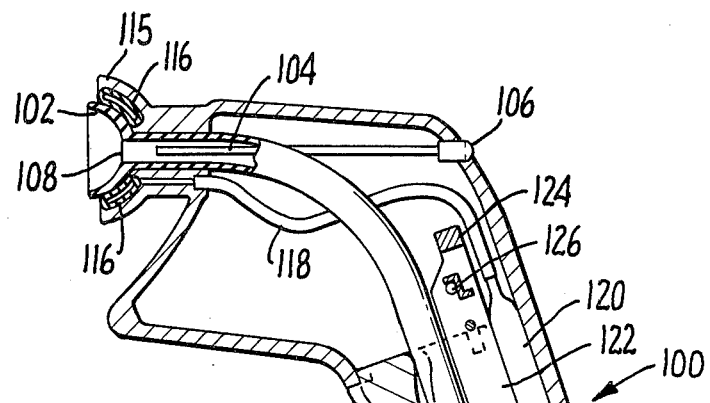
FIG. 8 is a side view, in section, of another embodiment of the invention wherein the soft lens cup is distorted by fluid pressure against a rigid outer cup.

The contact lens insertion tool is housed in a case 8 preferably of a tough plastic. The case includes a projection 10 which is preferably provided with an end piece 12 of a soft material such as sponge rubber. The case supports a lens cup 14 of a suitable size for the particular contact lens which is to be handled. Preferably the lens cup is slightly smaller in diameter than the lens so that the lens extends slightly beyond the edges of the cup. For instance, with a lens having a diameter of 16 mm a cup diameter of 14-15 mm is suitable, while with a smaller lens of 14 mm diameter, a cup diameter of from 12-13 mm is suitable. Obviously these sizes are for the relatively large soft contact lenses and will be substantially smaller for hard contact lenses. The cup 14 is made of a soft, yieldable, physiologically acceptable plastic such as polyolefin. Cup 14 has a central hole 16 and a tube 18 is connected to the hole. Tube 18 is of a rubber or plastic material which will hold its shape and which can be distorted to produce vacuum or pressure as is later brought out in detail.

The tool is provided with a rod 20 of a clear transparent material such as glass or suitable plastics or fiber optics, and the rod terminates at 22 just inside the opening 16. The distal end of the rod has a lens 24 thereon. The lens 24 serves to pick up ambient light and convey it through the light conveying rod 20 to the center opening 16 so that as the user holds the device up near his eye he will see a bright spot at the very center of the eye cup. Thus even a severely handicapped patient will have no trouble in properly locating cup 14 adjacent to the eyeball. The case 8 has a downwardly extending handle portion 9 and two sliding members are provided in the handle portion, namely, an upper member 26 which is suitably sized for actuation by a single finger, and a lower member 28 of a suitable size to be actuated by three fingers. Normally the thumb, not shown, would be wrapped around the back of the handle 9 and the index finger used to actuate the member 26 while the remaining three fingers would actuate the member 28. The lower member 28 is adjacent to the tube 18 and behind this is a fixed member 30 so that by pressing on the member 28 a substantial volume of air is discharged through the opening 16 due to the compression of tube 18.

The member 26 lies against tube 18 and on the opposite side of tube 18 is the member generally designated 32. The member 32 has a vertical portion 34 which normally lies behind tube 18 and a horizontal portion 36 which extends outside of the case 8 forming a button which can be actuated by a finger. Member 32 has pins 38 and 40 which are adapted to fit releasably into the clips 42 and 44 which are attached to the case 8. The number 26 has U-shaped arms 46 and 48 which lie on each side of the tube 18 and which have notches 50. The member 32 has pins 52 which form a loose fit in the notches 50 when the member 32 is in a lower position. The rear surface of member 32 is formed as a cam 54 which normally lies adjacent to the lower end of the curved arm 56. Arm 56 is pivoted at 58 and terminates in a forward end 60 lying adjacent the upper surface of a flexible cup 14. Mounted below cup 14 is a fixed arm 62. It is obvious that if arm 56 is pivoted in a counterclockwise direction, the cup 14 lying between the arm 60 and 62 will be somewhat distorted.

As is previously mentioned, member 32 can assume one of two positions and can be moved from one position to the other by means of the button 36 which extends from the case. The upper position is used for the insertion of a lens and the lower position in used for removal of the lens.

With member 32 in the upper position, it will be seen that the pins 38 and 40 engage the members 42 and 44 so that as one pushes backward, tube 18 will be compressed because of pressure on the tube between the member 26 and the forward surface 34. However, the lever arm 56 will not be displaced since the pins 52 are out of engagement with slots 50. Now one can apply pressure to 26, compressing tube 18 and then insert cup 14 into a holder which contains a contact lens. One now releases member 26 which causes a slight vacuum to form in tube 18 so that the lens will be picked up in cup 14. Now one places the member 12 against the cheek and brings the cup containing the contact lens toward the eye. The lens 24 will pick up and concentrate ambient light and transmit it through the tube 20 where it will show up as a bright spot in the center of cup 14, i.e. through hole 16. Thus, even an aphakic patient will have no problem in correctly orienting the lens with relation to the eye. Further, by resting the member 12 against the cheek, the whole assembly is very stable so that even a patient with poor coordination will have no difficulty in inserting the lens. As soon as the lens is in position on the eyeball, one now compresses the member 28 which causes a substantial amount of pressure to develop within tube 18 which breaks the adhesion between the cup 14 and the lens, causing the lens to be correctly inserted in the eye.

To remove the lens, one moves the button 36 to the lower position. This releases the pins 38 and 40 from members 42 and 44 and also drops pins 52 into the slots 50. With the parts in this position, it is apparent that the member 32 will move with the member 26 so that there will be no tendency for tube 18 to collapse. Further, in this position moving the member 26 to the rear will cause the cam surface 54 to contact the lever arm 56, rotating it in a counterclockwise direction. Now with the button 36 in the upper position, one compresses the tube by gripping the member 28 and moves the instrument toward the eye. When cup 14 contacts the lens, one releases member 28 which pulls a vacuum on tube 18 and the user also presses in on member 26 which causes the end 60 of lever 56 to press downwardly, distorting cup 14. This combination of the distortion of the cup 14 coupled with vacuum being applied thereto positively removes the lens from the eye. The lens can now be redeposited in a contact lens case. Thus, the entire operation of insertion and removal is accomplished without the hands ever touching the lens.

In some instances, patients have no trouble in removing the lens but great difficulty in inserting it. In such cases, a simplified form of the device can be employed as is shown in FIGS. 6 and 7. Basically, the parts are the same except that no means is provided for collapsing the cup, greatly simplifying the structure.

Thus, referring to FIGS. 6 and 7, case 70 has a generally horizontal portion 72 and a more or less vertical portion 74. A cheek rest 76 is provided as before and a lens cup 78 is held by tube 80. Tube 80 is connected to the flexible tube 82 and a light conducting rod 84 having a collector lens 86 extends into the tube 80. The center of cup 80 designated 88 thus receives light as previously described. Two pressure members 90 and 92 are provided, with 90 being much smaller than 92. The use of the device is substantially the same as was previously described for the insertion operation. One depresses button 90 partially collapsing tube 82, while the cup 78 is held over a contact lens in a case and button 90 is released, producing a slight vacuum in tube 82 which is sufficient to cause the lens to adhere to the cup 78. One now brings the cup 78 with the contact lens therein adjacent to the eye utilizing the cheek rest 76 to steady the device. The light through the opening 88 permits one to accurately locate the device. When the lens in the cup 78 has made contact with the eye, one presses on the member 92, producing a substantial pressure within tube 82 discharging the lens onto the eye.

Figure 9:
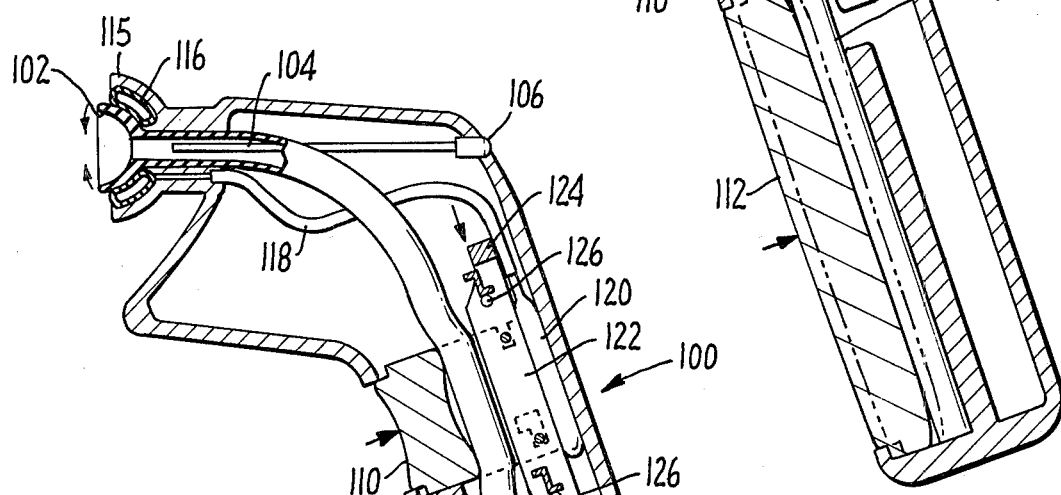
FIG. 9 is a view, similar to FIG. 8, showing the action of the parts when the cup is distorted.

The embodiment of the invention shown in FIGS. 8 and 9 is quite similar to that previously described in FIGS. 1-5 except that fluid pressure, either liquid or pneumatic, is employed to distort or collapse the lens cup. Thus, there is shown an insertion or removal device generally designated 100 having a soft lens cup 102 with a transparent rod 104 for directing ambient light from lens 106 to the hollow center 108 of the lens cup. The cup fits within a rigid shell 115. The tool is provided with an upper member 110 and the lower member 112 either or both of which can be squeezed as previously described. A flexible tube 114 lies behind the members 110 and 112 and leads to the hollow center 108 of lens cup 102.

Lying between the lens cup 102 and the shell 115 is an inflatable bladder 116 which is connected by means of tube 118 to a bulb 120. The device can be operated by any fluid and if the fluid is a gas it occupies the bulb 120, tube 118 and the bladder 116. Similarly, the chambers can be occupied by a liquid for hydraulic actuation.

Mounted behind the member 110 is the movable member 122 which is mounted in exactly the manner previously described for member 32. This member has an outwardly extending thumb piece 124 and when it is in the upper position, as is shown in FIG. 8, it is locked in place by pins 126 so that pressure on member 110 will exert pressure on tube 114 but will not exert pressure on bulb 120. Now if member 124 is moved downwardly, member 122 will be released so that pressure on member 110 will compress the bulb 120. Thus, as is shown in FIG. 9, this will expand the bladder 116 causing the eye cup 102 to become distorted in the direction shown by the arrows in FIG. 9, tending to dislodge a lens from the eye. This, of course, is accomplished by first putting pressure on member 112 and releasing it, causing a slight vacuum within the cup 102 as was previously described.

Figure 10:
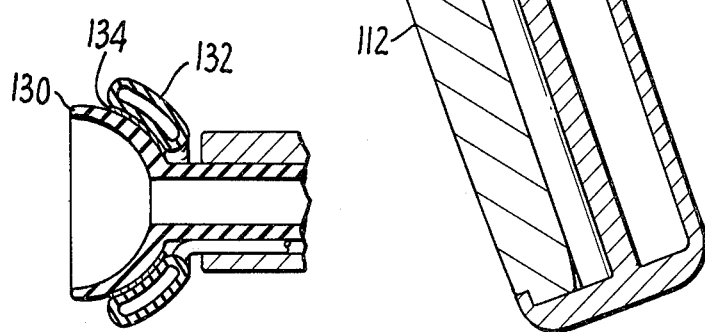
FIG. 10 is a partial side view of an alternate cup distortion device.

Instead of having a rigid shell surround the bladder, a structure such as shown in FIG. 10 may be employed. Here the soft lens cup 130 is surrounded by the flexible bladder 132 and the bladder and the cup are held together by means of adhesive 134. The other parts are as previously described. If the bladder 132 is now inflated, it will tend to distort the cup 130 somewhat after the fashion of a bi-metallic strip. Thus, in this structure, it is not necessary to employ the rigid outside shell but, of course, a protective covering can surround the soft cup if this is desired.

It is beieved apparent from the foregoing that I have provided an efficient device for inserting and removing contact lens and one which is particularly adapted for use by aphakic patients who may have poor coordination and steadiness.

I claim:

1. A contact lens insertion and/or removal device comprising in combination:
   a. a soft lens cup of a size adapted to receive a contact lens,
   b. an opening in the center of said cup, said opening leading to a tube,
   c. a rod of an optically clear material within said tube having a first end terminating near said opening and a second end having means for collecting light and directing the light through said rod,
   d. means for applying vacuum or pressure through said tube to said cup,
   e. a pair of arms adjacent to said lens cup,
   f. means for bringing said arms towards each other into contact with said lens cup to distort said cup,
   g. a member adapted to partially collapse said tube when in a first position and adapted to actuate one of said arms when in a second position, and
   h. means for bringing said member from said first position to said second position.

2. A contact lens insertion and/or removal device comprising in combination:
   a. a soft lens cup of a size adapted to receive a contact lens,
   b. an opening in the center of said cup, said opening leading to a tube,
   c. a rod of an optically clear material within said tube having a first end terminating near said opening and a second end having means for collecting light and directing the light through said rod,
   d. means for applying vacuum or pressure through said tube to said cup,
   e. an expandable, hollow chamber surrounding said soft lens cup, and
   f. means for applying a fluid pressure to said chamber whereby said lens cup will become distorted.

* * * * *